United States Patent
Springer

(10) Patent No.: US 9,364,527 B2
(45) Date of Patent: Jun. 14, 2016

(54) BOVINE VACCINES AND METHODS

(75) Inventor: Eric Springer, Canton, SD (US)

(73) Assignee: NOVARTIS TIERGESUNDHEIT AG, Basel (CH)

( * ) Notice: Subject to any disclaimer, the term of this patent is extended or adjusted under 35 U.S.C. 154(b) by 0 days.

(21) Appl. No.: 14/125,248

(22) PCT Filed: Jun. 8, 2012

(86) PCT No.: PCT/US2012/041443
§ 371 (c)(1),
(2), (4) Date: Dec. 10, 2013

(87) PCT Pub. No.: WO2012/170753
PCT Pub. Date: Dec. 13, 2012

(65) Prior Publication Data
US 2014/0105930 A1  Apr. 17, 2014

Related U.S. Application Data

(60) Provisional application No. 61/495,591, filed on Jun. 10, 2011.

(51) Int. Cl.
| | |
|---|---|
| *A61K 39/02* | (2006.01) |
| *A61K 39/102* | (2006.01) |
| *A61K 39/12* | (2006.01) |
| *A61K 39/155* | (2006.01) |
| *A61K 39/245* | (2006.01) |
| *A61K 39/00* | (2006.01) |

(52) U.S. Cl.
CPC .............. *A61K 39/0225* (2013.01); *A61K 39/02* (2013.01); *A61K 39/102* (2013.01); *A61K 39/12* (2013.01); *A61K 39/155* (2013.01); *A61K 39/245* (2013.01); *A61K 2039/521* (2013.01); *A61K 2039/545* (2013.01)

(58) Field of Classification Search
None
See application file for complete search history.

(56) References Cited

U.S. PATENT DOCUMENTS

| | | | |
|---|---|---|---|
| 2004/0043391 | A1 | 3/2004 | Utt et al. |
| 2004/0081666 | A1* | 4/2004 | Dominowski .............. 424/202.1 |
| 2007/0154943 | A1 | 7/2007 | Ellsworth et al. |
| 2009/0068223 | A1 | 3/2009 | Meyers et al. |
| 2009/0324641 | A1 | 12/2009 | Dominowski et al. |
| 2010/0266629 | A1 | 10/2010 | Dominowski et al. |

OTHER PUBLICATIONS

Novartis (http://www.cattlenetwork.com/cattle-resources/healthy-heifer/New-study-shows-Vira-Shield-HB-provided-12-month-duration-of-immunity-Against-Lepto-Hardjo-Bovis.html, pp. 1-5, accessed Jan. 3, 2015; available Feb. 24, 2011).*

Zuerner et al., A Leptospira Borgpetersenii Serovar Hardjo Vaccine Induces a Th1 Response, Activates NK cells, and Reduces Renal Colonization, Clin and Vaccine Immunol. 18:684-691. Feb. 2, 2011.

"Vira Shield Earns New Label Claim for 12-Month Duration of Immunity Against Lepto Hardjo-Bovis" (Mar. 6, 2011); Novartis Animal Health US, Inc., http://www.ah.novartis.com, p. 1-3.

* cited by examiner

*Primary Examiner* — Brian J Gangle
(74) *Attorney, Agent, or Firm* — David L. Pflugh

(57) ABSTRACT

Methods for stimulating immune responses in a bovine animal susceptible to infection by *Leptospira hardjo-bovis* are disclosed. In the methods, a composition of inactivated *L. hardjo-bovis* and an adjuvant is administered to the animal within about 4 weeks of birth. The immune responses stimulated in the animal prevent or shorten the duration of a subsequent *L. hardjo-bovis* infection. The immune response is effective for at least a year.

20 Claims, No Drawings

BOVINE VACCINES AND METHODS

This application is a 371 application of PCT/US2012/041443, filed Jun. 8, 2012, which claims benefit of provisional application 61/495,591, filed Jun. 10, 2011; the contents of which are incorporated by reference herein.

BACKGROUND

Leptospirosis is an infectious disease caused by bacteria from the genus *Leptospira*. The disease occurs in a variety of different animals and in humans. In cattle, leptospirosis can be chronic or acute. Chronic disease is generally caused by *Leptospira* that have "adapted" to cattle as a host. Cattle are said to be maintenance hosts for the cattle-adapted organisms. Chronic disease can manifest itself as abortions, stillbirths or birth of weak calves. Infertility may be a problem in chronically infected herds. Cattle infected with the host-adapted *Leptospira* may not completely clear the organisms from their bodies.

In contrast to chronic disease, acute disease is generally caused by *Leptospira* for which cattle are non-maintenance or incidental or hosts. Although symptoms of acute disease are generally severe, and in calves can be fatal, the leptospire organisms responsible are normally cleared from the bodies of animals that survive the disease.

Although there are over 200 pathogenic serovars of leptospires, five serovars, *hardjo, pomona, grippotyhposa, icterohaemorrhagiae* and *canicola*, are generally associated with cattle. Two of these serovars, *hardjo* and *pomona*, are generally associated with chronic disease, Hardjo serovars exist in two different species of *Leptospira*. Serovar *hardjo*, type *hardjo-bovis* is in the genus *Leptospira*, species *borgpetersenii* (referred to as *L. hardjo-bovis*). Type *hardjo-bovis* appears to be the major cause of chronic leptospirosis in cattle in the United States. Serovar *hardjo*, type *hardjo-prajitno* is in the genus *Leptospira*, species *interrogans*.

Compositions and methods that stimulate immune responses effective against *Leptospira* in cattle are known. However, attempts to stimulate protective and long-lasting immune responses can be less than satisfactory.

DETAILED DESCRIPTION

Compositions and methods for stimulating immune responses to *L. hardjo-bovis* in bovine animals are described. The compositions generally contain killed or inactivated *L. hardjo-bovis*, or extracts from *L. hardjo-bovis*. The compositions may contain an adjuvant. The immune responses obtained after administration of the compositions can be stimulated in animals of different ages, including young animals. The immune responses are generally long-lasting. In one example, compositions and methods for stimulating *L. hardjo-bovis*-specific immune responses in calves of about 4 weeks of age are described. The stimulated immune responses can be protective against a challenge of pathogenic *L. hardjo-bovis* when the challenge is initiated at least up to one year after administration of the immunostimulatory compositions. The immune responses can protect the animals from becoming chronically infected with *L. hardjo-bovis* or can decrease the duration of a chronic infection with *L. hardjo-bovis*. The compositions can stimulate the immune responses when the *L. hardjo-bovis* antigens are the only or majority of antigen in the composition. The compositions can also stimulate the immune responses when the *L. hardjo-bovis* antigens are combined with a number of other antigens in the composition. For example, the *L. hardjo-bovis* composition may be part of compositions containing antigens from other bacteria, from viruses, from a combination of other bacteria and viruses, as well as antigens from other infectious agents. Therefore, the compositions and methods can stimulate immune responses to *L. hardjo-bovis* with minimal or acceptable interference from other antigens in the composition.

The compositions are generally administered to bovine animals and stimulate one or more of specific and nonspecific immune responses. The immune responses generally prevent or reduce the probability that a bovine animal will be infected or will be chronically infected with *L. hardjo-bovis*. An animal administered the composition that becomes subsequently infected with *L. hardjo-bovis* generally will have a shorter duration of infection. The immune response stimulated by the composition and methods may make it possible or more likely that the bovine animals will clear the Leptospiral organisms from their bodies. Animals administered the disclosed compositions using the disclosed methods are less likely to display disease symptoms associated with infection of *L. hardjo-bovis*. For example, these animals are generally less likely to display symptoms associated with chronic infection of *Leptospira*, like abortions, stillbirths, birth of weak calves and/or infertility.

Administration of the disclosed compositions generally prevent or decrease the likelihood that *L. hardjo-bovis* is detected or isolated from the animal, for example in blood, urine or other tissues, after exposure to *L. hardjo-bovis* subsequent to the administration. The immune responses are generally effective for at least a year after administration. The disclosed compositions and methods for using the compositions can be used to stimulate or produce these immune responses in young animals. In one example, the animals may be as young as 4 weeks of age.

In one example, a method for stimulating an immune response to *L. hardjo-bovis*, preventing one or more of an infection, morbidity or disease in an animal susceptible to infection by *Leptospira*, comprises the steps of: administering to the animal within about 4 weeks of birth a first dose of a composition that includes inactivated *Leptospira* followed by administering to the animal a second dose of the composition that includes inactivated *Leptospira* about 4 weeks after administration of the first dose. In one example of the above method, the composition includes inactivated *Leptospira hardjo-bovis*. In another example of the above method, the composition further includes inactivated *Leptospira interrogans*, serovar *canicola* (referred to as *L. canicola*), *Leptospira interrogans*, serovar *grippotyphosa* (referred to as *L. grippotyphosa*), *Leptospira interrogans*, serovar *icterohaemorrhagiae* (referred to as *L. icterohaemorrhagiea*), *Leptospira interrogans*, serovar *pomona* (referred to as *L. interrogans*), or a combination thereof. In still another example of the above method, the composition further includes an adjuvant. In yet another example of the above method, the composition further reduces the systemic spread within the animal (leptospiremia), reduces the leptospire shedding in urine (leptospiruria), reduces the incidence and/or duration of *Leptospira* colonization in host animal tissues (e.g., the kidneys), or a combination thereof. In still another example of the above method, the composition further includes inactivated *Campylobacter fetus* to prevent disease or infection caused by *Campylobacter fetus*. In yet another example of the above method, the composition prevents disease caused by *Leptospira* in an animal susceptible to infection by *Leptospira* for a duration of at least 12 months after administration of the first or second dose. In yet another example of the above method, the animal may be selected from the group comprising a heifer, cow, bull, steer, calf and the like.

One example describes a method for stimulating an immune response in cattle comprising the steps of: administering to cattle within about 4 weeks of birth a first dose of a composition that includes inactivated *Leptospira* selected from the group comprising: *L. hardjo-bovis, L. canicola, L. grippotyphosa, L. icterohaemorrhagiae, L. pomona* or a combination thereof, followed by administering to cattle a second dose of the composition that includes inactivated *Leptospira* about 4-8 weeks after administration of said first dose. In one example of the above method, the composition further includes inactivated *Campylobacter fetus* to prevent disease or infection caused by *Campylobacter fetus*. In another example of the above method, the composition further includes inactivated bovine herpes virus-1 (BHV-1) to prevent disease or infection caused by BHV-1. In yet another example of the above method, the composition further includes inactivated bovine viral diarrhea (BVD) virus to prevent disease or infection caused by BVD. BVD may be type 1 or type 2, and may be cytopathic (CP) or noncytopathic (NCP). In yet another example of the above method, the composition further includes inactivated parainfluenza Type 3 ($PI_3$) to prevent disease or infection caused by $PI_3$. In still another example of the above method, the composition further includes inactivated bovine respiratory syncytial virus (BRSV) to prevent disease or infection caused by BRSV.

In another example of the above method, the composition further includes an adjuvant. In yet another example of the above method, the composition further reduces the systemic spread within the cattle (leptospiremia), reduces the leptospire shedding in urine (leptospiruria), reduces the incidence and/or duration of *Leptospira* colonization in host cattle tissues (e.g., the kidneys), or a combination thereof. In yet another example of the above method, the composition prevents disease caused by *Leptospira* in an animal susceptible to infection by *Leptospira* for a duration of at least 12 months after administration of the second dose. In yet another example of the above method, the composition prevents disease caused by BHV-1, $PI_3$, NCP BVD1, NCP BVD2, CP BVD1, BRSV or a combination thereof for a duration of at least 12 months after administration of the first dose or after administration of the second dose.

Immunogenic Compositions

This disclosure describes immunogenic compositions, immunostimulatory compositions, vaccine compositions and the like, and also describes methods of using the compositions to stimulate immune responses in a bovine animal that are effective against *L. hardjo-bovis*. The immune responses generally are specific for *L. hardjo-bovis*, but may be nonspecific. Generally, the immunogens or antigens in the composition will stimulate the host animal's immune system to make or increase a secretory, humoral, cellular antigen-specific, and/or other response. The specific immunogens can be proteins, polysaccharides, lipopolysaccharides, lipopeptides or other molecules; or it can be a combination of any of these or other immunogens. Other combinations are possible.

The disclosed compositions contain immunogens from *Leptospira borgpetersenii*, serovar *hardjo*, type *hardjo-bovis*, (*L. hardjo-bovis*). Generally, the *L. hardjo-bovis* is "inactivated" or "killed." Inactivated/killed generally refers to infectious agents (e.g., bacteria, viruses, other microorganisms or agents) that are not capable of reproducing or causing disease (i.e., avirulent). Inactivated bacterial preparations may be called bacterins. The inactivated/killed agents are able to stimulate an immune response when administered to an animal, in the context of a vaccine composition, for example. In contrast to inactivated vaccines, live vaccines and live attenuated vaccines, for example, are able to replicate and generally do so once they are administered to an animal. Another type of vaccine, called subunit vaccines, also does not replicate. Subunit vaccines generally contain substantially less than all of a bacterium or virus and, in this way, often may be distinguished from inactivated/killed vaccines. For example, subunit vaccines may contain single or a few recombinant protein antigens from a bacterium or virus. Subunit vaccines may also contain individual structures, like a capsid or capsomere from a virus, for example. Inactivated or killed vaccines generally include more of a bacterium or virus, for example, than does a subunit vaccine. For example, an inactivated vaccine may contain all or substantially all of a virus or bacterium. In one example, entire cultures of bacteria or viruses may be inactivated or killed. In another example, less than all, but still substantial parts of bacteria or viruses may be used in an inactivated/killed vaccine. For example, bacteria may be extracted with a chemical to obtain the cell wall, cell membrane or cell wall plus cell membrane portions that may be used as or in an inactivated/killed vaccine or immune stimulatory composition.

Generally, agents for inclusion in an inactivated or killed vaccine may be grown, purified or semi-purified, inactivated, and then formulated into a vaccine composition. Bacteria may be grown on cell free, serum-free, protein-free, synthetic medium and the like, using commonly known methods for growth of pure bacterial cultures. Often, bacteria are grown in liquid cultures. Viruses often are grown using cultured cells that are hosts for replication of the viruses. The bacteria or viruses may be purified, semi-purified, and/or concentrated. For example, bacteria grown in liquid culture may be subject to relatively low-speed centrifugation, the culture medium decanted, and the bacterial pellet re-suspended in buffer. Virus-infected cell cultures may be subjected to disruption to release cell-associated virus, and centrifugation to remove cellular debris. The remaining virus may be concentrated/ purified by a variety of methods like centrifugation, fractionation, chromatography, and the like.

The bacteria/viruses may be killed or inactivated using a variety of methods. In one example, the bacteria or viruses may be treated with various chemicals for various periods of time to render the agents incapable of replication, but still retaining at least some ability to stimulate an immune response (i.e., immunogenicity) when administered to an animal. Many such agents are known. Example inactivating agents include formalin/formaldehyde, ethyleneimine derivatives, ultraviolet radiation or heat, thimerosal and/or β-propiolactone, and others. The infectious agents are generally treated with a concentration of the agent for a length of time and at a temperature to inactivate the virus, yet still preserve at least some of the ability of the agent to be immunogenic and stimulate an immune response. Inactivating agents may be removed prior to formulation into compositions for administration to animals.

The inactivated or killed agent is normally formulated into a composition suitable for administration to an animal. The formulated composition contains an amount of the inactivated agent that is sufficient to stimulate an immune response in the animal to which it is administered. This amount of immunogen to be used may be determined by administering to an animal and then determining the immune response that is produced. This amount of agent or immunogen may be referred to, for example, as an immunogenic amount or immunostimulatory amount. There will generally be a range of the amount of immunogen over which an immune response will be produced in an animal. A specific minimum amount of an agent or immunogen may be needed before an immune response is produced. Administration of additional amounts of the immunogen, in excess of the minimum, in a composition likely will increase the extent of the immune response. At some input level of immunogen, it is likely that no increase in immune response would be obtained (i.e., saturation). Generally, an acceptable input amount of immunogen in a composition will be sufficient to stimulate an immune response in the animal to which the composition is administered. The amount of inactivated *Leptospira* that may be formulated into a composition may be such that between $1\times10^7$ and $1\times10^{10}$ organisms per dose are administered to a bovine animal. The amount of inactivated *Leptospira* may be $1\times10^7$, $5\times10^7$, $1\times10^8$, $5\times10^8$, $1\times10^9$, $5\times10^9$, or $1\times10^{10}$ organisms per dose, or amounts in between those numbers.

In addition to the inactivated agent, the composition may contain other components. In one example, the composition may contain one or more adjuvants. Adjuvant generally refers to substances that modulate immunogenicity of an immunogen or antigen. Adjuvants may enhance the magnitude, duration and/or specificity of an immune response to an immunogen. A variety of adjuvants exist. Adjuvants used in the disclosed compositions may include, but are not limited to, the RIBI adjuvant system (Bibi Inc.), alum, aluminum salts, such as aluminum hydroxide and aluminum phosphate, aluminum hydroxide gel; cholesterol, block co-polymers, other polymers such as POLYGEN®, DEAE, dextran, dextran sulfate, and methylacrylates, dimethylodecylammonium bromide, poxvirus proteins, Avridine lipid-amine adjuvant, lipid A, monophosoryl lipid A, animal oils (such as squalene), mineral oils (sold under the trademark DRAKEOL® and MONTANIDES®), vegetable oils (such as peanut, cottonseed, rapeseed, coconut oil), triterpenoid glycosides (such as saponin, Quil A, and QS21), detergents (such as polyoxyethylenesorbitan monooleate, sold under the trademark TWEEN® 80 and polyethylene oxide-polypropylene oxide block copolymers sold under the tradename PLURONIC®), bacterial component adjuvants (such as Freund's incomplete adjuvant, Freund's complete adjuvant, *Corynebacterium, Propionibacterium, Mycobacterium*, beat labile enterotoxin from *E. coli*, and cholera toxin), interleukins, monokines, interferons, liposomes, ISCOMs, synthetic glycopeptides (such as muramyl dipeptides and derivatives thereof), or combinations thereof.

The adjuvants can also be emulsions, specifically water in oil (W/O), oil in water (O/W) or multiphasic emulsions, like water/oil/water (W/O/W). Generally, the emulsions also contain surfactants. These adjuvants may be used in the Immunogenic compositions at concentrations ranging from 1-50%. The adjuvants may be used at concentrations of 5%, 10%, 15%, 20%, 25%, 30%, 35%, 40%, 45%, 50%, and at other and intermediate concentrations.

In addition, the compositions may include one or more pharmacologically acceptable carriers and/or vehicles that can be added to the immunogenic or vaccine compositions. For example, solvents, dispersion media, coatings, adjuvants, stabilizing agents, diluents, preservatives, antibacterial and antifungal agents, isotonic agents, adsorption delaying agents, binders, and the like, may be used. Diluents can include, but are not limited to, water, saline, dextrose, ethanol, glycerol (polypropylene glycol, polyethylene glycol, and others) and the like. Isotonic agents can include, but are not limited to, sodium chloride, dextrose, mannitol, sorbitol, lactose, and the like. Stabilizers can include, but are not limited to, albumin and the like.

A pharmaceutically acceptable vehicle, suitable for parenteral injection, is usually nontoxic and nontherapeutic. Examples of such vehicles are water, saline, Ringer's solution, dextrose solution, and Hank's solution. Nonaqueous vehicles, such as fixed oils, sesame oil, ethyl oleate, or triglycerides may also be used. Parenteral vehicles may also take the form of suspensions containing viscosity enhancing agents, such as sodium carboxymethylcellulose, sorbitol, or dextran. The vehicle may also contain minor amounts of additives, such as substances that enhance isotonicity and chemical stability, such as buffers and preservatives. Examples of buffers include phosphate buffer, bicarbonate buffer and tris buffer, while examples of preservatives include thimerosal, m- or o-cresol, formalin and benzyl alcohol. Standard formulations will either be liquid injectables or solids which can be taken up in a suitable liquid as a suspension or solution for injection. Thus, in a nonliquid formulation, the vehicle may comprise dextrose, human serum albumin, preservatives, etc., to which sterile water or saline could be added prior to administration.

Any pharmaceutically acceptable water soluble material or mixture of materials may be utilized in the disclosed compositions. The pharmaceutically acceptable water soluble material may comprise one or more monosaccharides, disaccharides, polysaccharides or carbohydrates. Examples include dextrose, mannitol, fructose, polyfructosan, polydextrose, dextrin, glucose, invert sugar, lactitol, lactose, isomalt, maltitol, maltose, maltodextrin, sorbitol, xylitol, sucrose, sucralose, mannose, galactose, xylose, arabinose, fructose, glucosamine, galactosamine, rhamnose, 6-O-methyl-D-galactose, 2-0-acetol-beta-D-xylose, 2-acetamido-2-dioxy-beta-D-galactose-4-sulphate, N-acetylglucosamine, iduronate, mannuronate, methyl galacturonate, galactose, arabinose, alpha-D-manopyranose and biopolymers formed by covalent bonding between one or more monosaccharide or disaccharide units. Examples of carbohydrates include alginate, amylose, cellulose, carrageenan, pectin. For convenience, monosaccharides, disaccharides, polysaccharides and carbohydrates may be collectively referred to as "sugars". Other pharmaceutically acceptable materials that are well known in the art may also be utilized.

Immunogens in Addition to *L. hardjo-bovis*

The disclosed compositions contain immunogenic amounts of inactivated *L. hardjo-bovis*. In one example, the disclosed compositions contain the inactivated *L. hardjo-bovis* as the only immunogens in the composition. In other examples, inactivated *L. hardjo-bovis* may be one of the immunogens in the composition; e.g., the composition may contain immunogens from one or more agents other than *L. hardjo-bovis*. These additional antigen or immunogen components may also be inactivated or killed agents, but not necessarily so. Generally in the art of vaccines, immunostimulatory compositions may contain immunogens from multiple agents. In this way, a single administration of a composition can result in production of immune responses to multiple agents.

If immunogens from other agents are added to the composition, immunogens from a variety of agents may be used. For example, immunogens from other species and/or serovars of *Leptospira* may be used. One or more of these species can be added to the composition. A composition may include immunogens from 2, 3, 4, 5 or more different *Leptospira* species and/or serovars. In one example, immunogens from *L. interrogans*, serovar *canicola, L. interrogans*, serovar *grippotyphosa, L. interrogans*, serovar *icterohaemorrhagiae, L. interrogans*, serovar *pomona* are combined with immunogens from *L. hardjo-bovis*. In one example, one or more of the *Leptospira* are inactivated. In one example, all of *Leptospira* in the composition are inactivated.

Other immunogens that may be added to the composition include immunogens from other bacteria and/or from viruses. In one example, immunogens from other bacteria are added. In one example, the immunogens are from *Campylobacter (Vibrio) fetus*. Bovine genital campylobacteriosis, previously known as vibriosis is a venereal disease of cattle caused by *Campylobacter (Vibrio) fetus*. *C. fetus* is an infectious bacterial disease of the genital tract causing infertility and abortions. It is a venereal disease spread by infected bulls when they mate susceptible cows and heifers or by artificial insemination if pipettes or semen are contaminated. It is considered to be an important cause of infertility in cattle. In one example, the *C. fetus* immunogens or antigens may be added to a composition containing immunogens from *L. hardjo-bovis, L. canicola, L. grippotyphosa, L. icterohaemorrhagiae* and *L. pomona*.

In one example, immunogens from viruses are added to the composition. Immunogens from many different bovine viruses can be used. Some examples include immunogens from cytopathic or noncytopathic bovine virus diarrhea type 1 (BVD1), cytopathic or noncytopathic bovine virus diarrhea type 2 (BVD2), parainfluenza type 3 (PI$_3$), bovine respiratory syncytial virus (BRSV) or bovine herpes virus-1 (BHV-1).

Bovine viral diarrhea (BVD) virus is a troublesome disease complex that affects both dairy and beef cattle. Bovine viral diarrhea virus consists of hundreds of different strains, making bovine viral diarrhea both difficult to control and economically disastrous for producers. Bovine viral diarrhea virus causes costly respiratory and reproductive diseases. The most economically devastating impact of bovine viral diarrhea is the birth of persistently infected animals from dams infected with noncytopathic BVD. The strains of BVD disclosed include, but are not limited to noncytopathic bovine virus diarrhea type 1 (NCP BVD1), noncytopathic bovine virus diarrhea type 2 (NCP BVD2) and cytopathic BVD1 (CP BVD1).

The Parainfluenza Type 3 or PI$_3$ virus is relatively common in cattle and is found worldwide. Affected animals exhibit watery to yellow-colored discharges from the eyes and nose, coughs, increased respiration rates and fever. By itself, PI$_3$ is a relatively mild infection and death due to the disease is rare. However, PI$_3$ generally works in concert with IBR, BVD, BRSV, *pasteurella* pneumonia and *Histophilus somni* infections, making the mixed infections more damaging and dangerous. As with most diseases, calves are the most susceptible to PI$_3$.

Bovine Respiratory Syncytial Virus (BRSV) is the etiologic agent of a specific viral respiratory disease of cattle of all ages, including nursing calves. Infection is characterized by rapid breathing, coughing, loss of appetite, discharge from the nose and eyes, fever, and swelling around the throat and neck. In an acute outbreak, deaths may follow rapidly after onset of signs. Pathology of BRSV typically consists of subpleural and interstitial emphysema with consolidating lesions characteristic of pneumonia. Clinically, BRSV infection may be indistinguishable from other viral infections associated with the bovine respiratory disease complex. Exacerbation of clinical signs has been documented when concurrent BRSV and BVD or IBR infection exists.

Bovine herpes virus 1 (BHV-1) is a virus that causes several diseases worldwide in cattle, including rhinotracheitis, vaginitis, balanoposthitis, abortion, conjunctivitis, and enteritis. BHV-1 is also a contributing factor in shipping fever. BHV-1 is spread through sexual contact, artificial insemination, and aerosol transmission. Like other herpes viruses, BHV-1 causes a lifelong latent infection and shedding of the virus. The sciatic nerve and trigeminal nerve are the sites of latency. BHV-1 also causes a generalized disease in newborn calves, characterized by enteritis and death. The respiratory disease caused by BHV-1 is commonly known as infectious bovine rhinotracheitis.

Infectious bovine rhinotracheitis (commonly called IBR or red nose) is an acute, contagious virus disease of cattle which is often implicated as an infection which initiates the shipping fever complex. This infection usually occurs in the air passages of the head and the wind pipe. However, in females this virus also causes inflammation of the vulva and vagina and may result in abortion. Cattle of all ages that have not been vaccinated or have not recovered from the disease are susceptible to IBR.

In one example of the disclosure, a combination of inactivated *Leptospira hardjo-bovis, Leptospira canicola, Leptospira grippotyphosa, Leptospira icterohaemorrhagiae* and *Leptospira pomona* may be referred to as L5$^{HB}$. in another example, the L5$^{HB}$ may contain *Campylobacter fetus* and may be referred to as VL5$^{HB}$. In another example of the disclosure, a combination of inactivated BHV-1 PI$_3$, NCP BVD1, NCP BVD2, CP BVD1 and BRSV may be referred to as VIRA SHIELD® 6. A composition containing the 5 *Leptospira* bacterins, the *C. fetus* bacterin, and VIRA SHIELD® 6 (6 inactivated viruses and adjuvant) may be referred to as VIRA SHIELD® 6+VL5$^{HB}$. All of these compositions are sold by Novartis Animal Health US, Inc., Greensboro, N.C., USA. Non-limiting examples of pathogens and immunomodulatory molecules from which additional immunogens may be selected include, but are not limited to: *Mannheimia haemolytica*; *Histophilus somni* (previously *Haemophilus somnus*); rotavirus (BRV); coronavirus (BCV); *Mycoplasma bovis; Neospora caninum; Trichomonas* spp.; *Vibrio*; Clostridial antigens; *Pasteurella multocida; Fusobacterium necrophorum; E. coli* O 157:H7; *Salmonella enterica* and others.

Generally, addition to the composition of immunogens other than *L. hardjo-bovis* does not result in a decrease or in a significant decrease of the immune response to the *L. hardjo-bovis* immunogens in the animal. Even in compositions that contain multiple immunogens other than *L. hardjo-bovis*, immune responses active against *L. hardjo-bovis* are produced and are effective in the animal. Therefore, antigenic interference, of the type that would render the composition unable to stimulate an immune response effect against *L. hardjo-bovis*, generally do not occur through use of the disclosed compositions.

Administration

"Administering" or "administration" includes any method of contacting an animal with a composition in a manner that can lead to an immune response to the composition in the animal. Herein, administration of the disclosed composition refers to a vaccine or immunogenic composition and may be referred to as immunization. Various methods of administering may be used and may include parenteral, oral, intranasal, aerosol and the like. Parenteral administration may include intramuscular, subcutaneous, intravenous, intradermal and the like. In one example, the compositions of the disclosure can be administered via an injection in intramuscular, subcutaneous, transdermal, intradermal or subdermal routes. However, it is also possible that the compositions can be administered via other routes, such as oral, intranasal, intralymph node, intradermal, intraperitoneal, mucosal tissue uptake, rectal, transdermal, or vaginal routes of administration or a combination thereof. The route of administration may depend on the animal being vaccinated, vaccination history and convenience of the person administering the vaccine.

Generally, administration of the compositions may be given to animals as young as a few weeks of age. In various examples, calves 2 weeks, 3 weeks, 4 weeks, 5 weeks, 6 weeks, 7 weeks, 8 weeks, 10 weeks, 12 weeks, 14 weeks, 16 weeks, 18 weeks, 20 weeks, 22 weeks, 24 weeks, 26 weeks or more, of age may be administered the compositions. Animals between about 4 to 26 weeks of age may be administered the compositions. Adult animals can also be administered the compositions.

Administration of the composition may be given more than once. Multiple administrations over a period of time may better facilitate production of an immune response. Repeated vaccinations are preferable at periodic time intervals to enhance the immune response initially or after a long period of time since the last dose. The time interval between vaccinations varies depending on the age and condition of the animal.

As used herein, the term "first dose" refers to the first administration of a composition to an animal in a manner that can lead to an immune response to the composition. As used herein, the term "second dose" refers to the second administration of a composition to an animal in a manner that can lead to an immune response to the composition. Administration of a first dose and a second dose may be referred to as administered twice. As used herein, the term "booster" refers to a second or any subsequent administration of a previously administered composition. The period of time between a first dose and a second or any booster dose, may vary. This period of time may be between 1 week and 52 weeks. In one example, the period may be 4-8 weeks. In one example, the period may be 4, 5, 6, 7, 8, 9, 10, or more weeks. In one example, the period of time may be 4 weeks. To insure sustained high levels of an immune response, it may be helpful to re-administer a booster immunization to the host animals on a periodic basis. This periodic basis may range from monthly, to every six months, to yearly, to multiple years. In one example, the compositions are administered annually.

In one example, the animals are administered a first dose at between about 4 to 26 weeks of age, and is followed, within about 4 weeks later, 8 weeks later, or 4 to 8 weeks later, by a second dose or administration.

Immune Response

Administration of the disclosed compositions is designed to produce or stimulate an immune or immunological response in the recipient. The immune response generally will prevent or reduce infection with infectious agents whose immunogens are included in the compositions. Because administration stimulates an immune response that is protective, the process may be referred to as vaccination. The immune response can be transient, but generally is long-acting. The intent of vaccination is to stimulate an immune response that confers a degree of protection limiting infection and/or disease caused by exposure to *Leptospira hardjo bovis*, and to agents related to other immunogens included in the compositions.

Generally, an immune or immunological response is the development of a cellular, antibody-mediated, and/or other immune response. Usually, this response includes but is not limited to one or more of the following effects; the production or stimulation of antibodies, B cells, helper T cells, suppressor T cells, and/or cytotoxic T cells and/or γδT cells, directed specifically to an antigen or antigens included in the composition or vaccine of interest. There are many components that can result in the immune responses as defined by antibodies, B cells, T cells and the like. Measurement of these components may be used to infer whether or not a humoral, cellular, combination of humoral and cellular, or other response exists, is stimulated or is changed.

Immune responses effective against leptospiral immunogens may confer a degree of protection limiting infection and/or disease caused by exposure to *Leptospira hardjo-bovis, Leptospira canicola, Leptospira grippotyphosa, Leptospira icterohaemorrhagiae* and *Leptospira pomona*. Vaccination has the potential to mitigate leptospiral infection in multiple ways, including reducing systemic spread within the animal (leptospiremia), reducing leptospire shedding in urine (leptospiruria) and reducing the incidence and/or duration of *Leptospira* colonization in host animal tissues. Vaccination may also facilitate clearance of the infecting agents from the bodies of animals.

For example, immune responses produced in bovine animals in response to administration of the disclosed compositions may prevent or reduce "systemic spread," referring to the spread of an infection from one system or organ to an additional system or organ. As used herein, "shedding" refers to the excretion of an infectious agent (i.e. viruses, bacteria, fungi, protozoa, multicellular organisms, etc.) from the body of an infected host. As used herein, the term "colonization" refers to the establishment of an infection by an infectious agent within a host. Colonization may occur within cells, tissues, organs, or systems.

Immune responses stimulated by the disclosed compositions and methods can be determined by a variety of methods. In one example, bovine animals are administered the immunogenic compositions and, subsequently, infectious *L. hardjo-bovis* is administered to the animals as a challenge. The effects of the challenge are measured. For example, subsequent to administration of the vaccine composition, pathogenic amounts of *L. hardjo-bovis* may be administered to the animals. Administration of pathogenic amounts of *L. hardjo-bovis* may generally be given any time subsequent to administration of the immunogenic compositions. Generally, however, it may take a few weeks for the animals to mount an immune response to the vaccine. This pathogenic amount of *L. hardjo-bovis*, in absence of administration of the vaccine composition, would normally produce a measurable effect which would be less or nonexistent in vaccinated animals. In one example, vaccinated bovine animals, and nonvaccinated control bovine animals, are both administered a pathogenic challenge of *L. hardjo-bovis*. Subsequent to administration of the challenge, tissue samples are obtained from both the vaccinated and unvaccinated animals and presence of the *L. hardjo-bovis* challenge organisms in the samples is determined, using a variety of possible methods. Due to stimulation of an immune response specific for *L. hardjo-bovis* in the vaccinated animals, the result is that detection of *L. hardjo-brevis* in tissues from the vaccinated animals is less frequent than in tissues from the animals that were not vaccinated. Tissue samples may be obtained from the animals any time up to 1 year subsequent to administration of the immunogenic compositions, and tested for presence of the administered *L. hardjo-bovis* challenge. In one example, animals are administered a *L. hardjo-bovis* challenge between about 30 to 56 weeks subsequent to administration of the vaccine, and presence of challenge organisms in animal tissues (i.e., morbidity) is subsequently determined. In one example, the vaccinated animals have a reduced rate of *L. hardjo-bovis* morbidity as compared to unvaccinated animals. In one example, detection of the *L. hardjo-bovis* challenge organisms in tissues of the vaccinated animals is 25%, 40%, or 50% less likely than in tissues of the unvaccinated animals. Such studies generally assess the ability of animals to clear the challenge organisms from the body.

The results from studies of this type may be correlated with other studies, that may be easier, cheaper, faster, etc. to conduct. These other studies may be referred to as potency studies or assays, since they also measure the ability of the compositions to stimulate a relevant immune response effective against *L. hardjo-bovis*. Various potency assays may be employed. In one example, the vaccine compositions are administered to bovine animals and various immunological parameters are subsequently measured (e.g., levels of antibodies specific for *L. hardjo-bovis*). Levels of these antibodies, for example, may be correlated to results of challenge studies. In this way, subsequent studies may measure immunological responses due to administration of the vaccine, and potency of the vaccine may be inferred from levels of the immune response (i.e., a challenge study is avoided). In some cases, results in non-bovine animal models may be correlated with the results in bovine models, subsequently eliminating use of the bovine model. In some cases, it may be possible to correlate in vitro assays with the results in bovine models, thereby eliminating the use of an animal model altogether. Various known methods and assays may be used in this way to assess the potency of the immunogenic or vaccine compositions.

EXAMPLES

The examples are for the purpose of illustrating an example and are not to be construed as illustrating limitations.

Example 1

*Leptospira* Vaccine Organisms, Growth and Preparation

*Leptospira borgpetersenii* serovar *hardjo*, type *hardjo-bovis*, isolate GL667 was used in vaccine compositions. This isolate was cultured from cattle urine received at Grand Laboratories, Inc. Liquid cultures of *L. hardjo-bovis* for use in vaccine compositions were grown in Lepto medium supplemented with Bovine Serum Albumin and polyoxyethylene-sorbitan monooleate, sold under the trademark TWEEN® 80 and adjusted to pH 7.4. Cultures were grown at 30° C. with agitation and/or aeration for 3 to 15 days. Cultures were harvested when they had reached a minimum growth of 50 nephelometer units (ntu). Prior to inactivation, the number of cells per ml of culture was determined. The cultures were concentrated by ultrafiltration and inactivated by adding formaldehyde. The pH of the inactivated cultures were adjusted to 6.5-5.5. Thimerosal was added as a preservative. The concentrated, inactivated, preservative-added mixtures were referred to as bacterins.

Other *Leptospira* serovars used in vaccine compositions include: *L. interrogans*, serovar *canicola*, *L. interrogans*, serovar *grippotyphosa*, *L. interrogans*, serovar *icterohaemorrhagiae*, and *L. interrogans*, serovar *pomona*.

These *Leptospira* organisms were grown and prepared similar to *L. hardjo-bovis*, as described above.

Example 2

Formulation of *Leptospira* Composition

A vaccine composition containing bacterins from the 5 *Leptospira* species described in Example 1 was formulated. The minimum per dose concentrations of bacterins described in Example 1 that were administered to animals was: *L. borgpetersenii* serovar *hardjo*, 500 nephelometer units; *L. interrogans*, serovar *canicola*, $1\times10^8$ organisms; *L. interrogans*, serovar *grippotyphosa*, $1\times10^9$ organisms; *L. interrogans*, serovar *icterohaemorrhagiae*, $1\times10^8$; and *L. interrogans*, serovar *pomona*, $5\times10^8$ organisms. The final formulation was prepared by combining the bacterins with mineral oil and emulsifiers and passing the mixture through a Microfluidics high pressure homogenizer. The amount of mineral oil and emulsifier added was such that the final concentration resulted in an oil in water emulsification following homogenization This compositions containing the 5 *Leptospira* bacterins and adjuvant, is referred to as "L5$^{HB}$."

Example 3

*Campylobacter fetus* Vaccine Organisms, Growth and Preparation

*Campylobacter fetus* strain 16661, isolate GL 131 was used in vaccine compositions. *C. fetus* was grown in *Vibrio* Fetus Broth Media (*Brucella* Broth supplemented with yeast and succinic acid and adjusted to pH 7.0±0.2). Liquid cultures were grown at 35-39° C. with agitation and/or aeration for 12 to 96 hours. The pH of the culture was monitored and cultures were harvested when pH of the cultures increased and reached 7.4-7.9. Cultures were inactivated with 0.4±0.1% formaldehyde and incubated at 35-39° C. for 24±4 hrs. The pH of inactivated cultures was adjusted to 7.2±0.2 with sodium hydroxide or nitric acid. The inactivated, pH-adjusted mixtures were referred to as bacterins.

Example 4

Formulation of Combination *Leptospira* and *Campylobacter fetus* Composition

*C. fetus* bacterins, when included in vaccine compositions, were formulated with compositions containing the 5 *Leptospira* species (L5$^{HB}$) described in Example 2. The minimum per dose concentrations in such a composition was: *C. fetus*, 0.9 OD$_{600\ nm}$ units, *L. hardjo-bovis*, 500 nephelometer units; *L. canicola*, $1\times10^8$ organisms; *L. grippotyphosa*, $1\times10^9$; *L. icterohaemorrhagiae*, $1\times10^8$ and *L. pomona*, $5\times10^8$ organisms. The final formulation was prepared by combining the bacterins with mineral oil and emulsifiers and passing the mixture through a Microfluidics high pressure homogenizer. The amount of mineral oil and emulsifier added was such that the final concentration resulted in an oil in water emulsification following homogenization. This composition, containing the 5 *Leptospira* bacterins, the *C. fetus* bacterin and adjuvant is referred to as "VL5$^{HB}$."

Example 5

Formulation of Combination *Leptospira*, *Campylobacter* and Viral Compositions

In some cases, the composition containing the 5 *Leptospira* species (L5$^{HB}$; described in Example 2), or the composition containing the 5 *Leptospira* species and the *C. fetus* (VL5$^{HB}$; described in Example 4) was combined with antigens from 6 different viruses that are known as VIRA SHIELD® 6. VIRA SHIELD® 6 contains 6 inactivated viruses: noncytopathic bovine virus diarrhea type 1. (NCP BVD1), noncytopathic bovine virus diarrhea type 2 (NCP BVD2), cytopathic BVD1

(CP BVD1), parainfluenza type 3 (PI3), bovine respiratory syncytial virus (BRSV) and bovine herpes virus-1 (BHV-1). The final formulation was prepared by combining the inactivated viruses and bacterins with mineral oil and emulsifiers and passing the mixture through a Microfluidics high pressure homogenizer. The amount of mineral oil and emulsifier added was such that the final concentration resulted in an oil in water emulsification following homogenization. The amount of each inactivated virus used to create the vaccine composition was determined using relative potency assays. The relative potency assays determined a threshold level of immune response produced by the vaccine, or determined the survival of vaccinated animals to challenge with known amounts of pathogenic viruses. The composition containing the 5 Leptospira bacterins, the C. fetus bacterin, and VIRA SHIELD® 6 (6 inactivated viruses and adjuvant) is referred to as "VIRA SHIELD® 6+VL5$^{HB}$."

Example 6

Clinical Study

A vaccine animal challenge study was performed. Briefly, 4 week old calves were vaccinated with a composition containing L. hardjo-bovis bacterin (L5$^{HB}$) and were then challenged, about 1 year later, with live, pathogenic L. hardjo-bovis. Vaccinated, and unvaccinated control animals, were followed post-challenge to determine effectiveness of the immunization. More details of the study are described below.
Test and Control Vaccines A test vaccine containing L. hardjo-bovis bacterins was used. The vaccine was VIRA SHIELD® 6+VL5$^{HB}$ as described in Example 5. The vaccine contained 500 ntu/dose of L. hardjo-bovis bacterin. Animals receiving the test vaccine may be referred to as the vaccine group. The control vaccine was VIRA SHIELD® 6. Animals receiving the control vaccine may be referred to as the placebo control.
Vaccination The test and the control vaccines were administered to 20 4-week-old dairy Holstein heifers on Day 0 (primary immunization). Twenty-eight days later (Day 28), the animals received a second administration of the test and control vaccines (booster immunization). The vaccines were administered subcutaneously in the necks of the animals, in a volume of 5.0 ml.
Challenge Beginning 369 days after the booster immunizations (Day 397), all study calves were challenged with the same pool of L. hardjo bovis challenge material. Live, log-phase L. borgpetersenii serovar hardjo type hardjo-bovis was diluted to $10^7$ organisms per ml. One-half ml was administered via the intraocular route (0.5 ml per each conjunctival sac, for a total dose of 1 ml). This dose was administered to the calves each day for 3 consecutive days (Days 397-399).

Prior to challenge, seven calves were excluded from the study. All seven calves were either found dead or required euthanasia, and all instances were determined to be unrelated to vaccination.
Results—General Beginning prior to vaccination, and continuing until 57 days after the first challenge (Day 454), various blood and urine samples were obtained from the calves and clinical observations of the calves were conducted. For animals found dead during the study, and on day 57 after the first challenge for the surviving animals, the calves were necropsied, and kidney, uterus, ovary and oviduct samples were obtained.

The primary outcome of the study was morbidity as determined by post-challenge detection of L. hardjo-bovis organisms in the blood, urine and/or tissue samples. Organism detection was attempted and determined by culturing of organisms from the blood, urine and tissue samples. Fluorescent antibody detection of organisms in concentrated urine samples was also attempted. Polymerase chain reaction (PCR) detection in urine was used in some cases. Tissue samples used included samples from reproductive tissue (i.e., uterus, ovary and oviducts). Secondary outcomes measured in the study included clinical observations of inappetance/anorexia, depression, jaundice, diarrhea and conjunctivitis. Composite morbidity was determined, based on detection of L. hardjo-bovis in any of the above described samples and by any of the above listed methods. In addition, individual analyses were performed, as described below, based on various samples, or based on various samples and method of detection.

In addition to tabulation of morbidity, Preventive Fraction was calculated to determine the percentage of animals in which vaccination resulted in no morbidity, as compared to animals that were not vaccinated. Preventive Fraction was estimated along with the corresponding 95% confidence intervals (including lower confidence bound (LCB)) for proportion of morbid animals caused by L. hardjo-bovis infection if: (1) any of the post-challenge urine samples collected during the study tested positive by isolation by FA; (2) any of the post-challenge kidney tissue samples harvested at the end of the study tested positive by isolation; (3) if any of the post-challenge reproductive tissue samples harvested at the end of the study tested positive by isolation. Composite (all of the above) as well as individual analyses were performed.

Secondary outcomes included non-pathognomic, clinical observations of inappetence/anorexia, depression, jaundice, diarrhea and conjunctivitis.

Primary Outcome Results—Composite

Morbidity, as determined by all methods (composite morbidity is summarized in Table 1.

TABLE 1

Frequency (Row Percent) Total Morbid Calves by Treatment (Per Protocol Definition)

| Treatment Group | Outcome | | Total Number |
|---|---|---|---|
| | Morbid | Not Morbid | |
| Vaccine Group | 5 (27.78%) | 13 (72.22%) | 18 |
| Placebo Control | 18 (100.00%) | 0 (0.00%) | 18 |
| Total | 23 | 13 | 36 |

The vaccinate group showed a statistically significant lower proportion of morbid animals compared to the placebo control group (p<0.0001; Fisher's Exact Test).

Preventive Fraction, for animals testing positive post-challenge by urine fluorescent antibody, or urine, kidney tissue or reproductive tissue reisolation (composite), is shown in Table 2.

TABLE 2

Preventive Fraction and Lower and Upper 95% Confidence Bounds of Total Morbid Calves[1]

| Total Number | | Morbid per Group | | Preventive Fraction | Confidence Bound | |
|---|---|---|---|---|---|---|
| Vaccines | Controls | Vaccines | Controls | | Lower | Upper |
| 18 | 18 | 5 | 18 | 0.72 | 0.47 | 0.90 |

[1]Animals testing positive post-challenge by urine fluorescent antibody, kidney tissue or reproductive tissue Preventive Fraction was 0.72 (LCB=0.47) for the vaccine group.

Primary Outcome Results—Individual

Reisolation/Fluorescent Antibody Detection of Organisms in Urine:

For the first set of individual analyses, a calf was classified as being morbid if it exhibited infection caused by *L. hardjo bovis* post-challenge by total shedding from urine as identified by either re-isolation or fluorescent antibody detection. Table 3 shows outcome (morbid/not morbid) versus treatment group for the analysis.

TABLE 3

Frequency (Row Percent) Morbid Calves by Total Urine Shedding by Treatment (As defined by urine reisolation or fluorescent antibody test)

| Treatment Group | Outcome | | Total |
|---|---|---|---|
| | Morbid | Not Morbid | Number |
| Vaccine Group | 5 (27.78%) | 13 (72.22%) | 18 |
| Placebo Control | 18 (100.00%) | 0 (0.00%) | 18 |
| Total | 23 | 13 | 36 |

The vaccinate group showed a statistically significant lower proportion of morbid animals compared to the placebo control group (p<0.0001: Fisher's Exact Test).

Preventive Fraction for the protocol definition of morbid animals by total shedding is shown in Table 4.

TABLE 4

Preventive Fraction and Lower and Upper 95% Confidence Bounds of Morbid Calves by Total Shedding[1]

| Total Number | | Morbid per Group | | Preventive Fraction | Confidence Bound | |
|---|---|---|---|---|---|---|
| Vaccines | Controls | Vaccines | Controls | | Lower | Upper |
| 18 | 18 | 5 | 18 | 0.72 | 0.47 | 0.90 |

[1]Animals testing positive post-challenge by urine FA, kidney tissue or reproductive tissue Preventive Fraction was 0.72 (LCB=0.47) for the vaccine group.

Fluorescent Antibody Detection of Organisms in Urine:

For the next set of analyses, animals were classified as positive for morbidity if any of the post-challenge urine samples collected during the study tested positive for *L. hardjo bovis* using fluorescent antibody detection. Table 5 shows outcome (morbid/not morbid) versus treatment group for the analysis.

TABLE 5

Frequency (Row Percent) of Morbid Calves by Urine FA

| Treatment Group | Outcome | | Total |
|---|---|---|---|
| | Morbid | Not Morbid | Number |
| Vaccine Group | 1 (5.56%) | 17 (94.44%) | 18 |
| Placebo Control | 12 (66.67%) | 6 (33.33%) | 18 |
| Total | 13 | 23 | 73 |

The vaccinate group showed a statistically significant lower proportion of animals with positive Urine FA tests compared to the placebo control group (p=0.0003; Fisher's Exact Test).

Preventive Fraction for the urine infection by FA is presented in Table 6.

TABLE 6

Preventive Fraction and Lower and Upper 95% Confidence Bounds of Morbid Calves by Urine FA[1]

| Total Number | | Morbid per Group | | Preventive Fraction | Confidence Bound | |
|---|---|---|---|---|---|---|
| Vaccines | Controls | Vaccines | Controls | | Lower | Upper |
| 18 | 18 | 1 | 12 | 0.92 | 0.59 | 1.00 |

[1]Any positive post-challenge urine samples by fluorescent antibody test

Preventive Fraction was 0.92 (LCB=0.59) for the vaccine group.

Reisolation of Organisms in Urine:

For the next set of analyses, animals were classified as positive for morbidity if *L. hardjo bovis* was reisolated from any of the post-challenge urine samples collected during the study. Table 7 shows outcome (morbid/not morbid) versus treatment group.

TABLE 7

Frequency (Row Percent) of Morbid Calves by Urine RI

| Treatment Group | Outcome | | Total |
|---|---|---|---|
| | Morbid | Not Morbid | Number |
| Vaccine Group | 4 (22.22%) | 14 (77.78%) | 18 |
| Placebo Control | 18 (100.00%) | 0 (0.00%) | 18 |
| Total | 22 | 14 | 36 |

The vaccinate group showed a statistically significant lower proportion of animals with positive Urine RI tests compared to the placebo control group (p<0.0001; Fisher's Exact Test).

Preventive Fraction for the urine infection by reisolation is presented in Table 8.

TABLE 8

Preventive Fraction and Lower and Upper 95% Confidence Bounds of Morbid Calves by Urine RI[1]

| Total Number | | Morbid per Group | | Preventive Fraction | Confidence Bound | |
|---|---|---|---|---|---|---|
| Vaccines | Controls | Vaccines | Controls | | Lower | Upper |
| 18 | 18 | 4 | 18 | 0.78 | 0.52 | 0.94 |

[1]Any positive post-challenge re-isolation of organisms from urine

Preventive Fraction was 0.78 (LCB=0.52) for the vaccine group.

Reisolation of Organisms from Kidney:

For the following analysis, animals were classified as positive for kidney infection caused *L. hardjo bovis* if post-challenge kidney tissue samples harvested at the end of the study tested positive by isolation. Table 9 shows outcome (morbid/not morbid) versus treatment group.

TABLE 9

Frequency (Row Percent) of Morbid Calves by Kidney Infection

| Treatment Group | Outcome | | Total Number |
|---|---|---|---|
| | Morbid | Not Morbid | |
| Vaccine Group | 0 (00.00%) | 18 (100.00%) | 18 |
| Placebo Control | 18 (100.00%) | 0 (00.00%) | 18 |
| Total | 18 | 18 | 36 |

The vaccinate group showed a statistically significant lower proportion of animals with positive kidney tissue tests compared to the placebo control group (p<0.0001; Fisher's Exact Test), Preventive Fraction for kidney infection is presented in Table 10.

TABLE 10

Preventive Fraction and Lower and Upper 95% Confidence Bounds of Morbid Calves by Kidney Infection[1]

| Total Number | | Morbid per Group | | | Confidence Bound | |
|---|---|---|---|---|---|---|
| V[2] | C[3] | V | C | PF[4] | Lower | Upper |
| 18 | 18 | 0 | 18 | 1.00 | 0.81 | 1.00 |

[1]Calves having positive kidney tissue results post challenge
[2]Vaccine group
[3]Placebo control
[4]Preventive fraction Preventive Fraction was 1.00 (LCB=0.81) for the vaccine group.

Reisolation of Organisms from Reproductive Tissue:

For the following analysis, animals were classified as positive for reproductive infection caused *L. hardjo bovis* if post-challenge reproductive tissue samples harvested at the end of the study tested positive by isolation. Table 11 shows outcome (morbid/not morbid) versus treatment group.

TABLE 11

Frequency (Row Percent) of Morbid Calves by Reproductive Tissue Infection.

| Treatment Group | Outcome | | Total Number |
|---|---|---|---|
| | Morbid | Not Morbid | |
| Vaccine Group | 0 (00.00%) | 18 (100.00%) | 18 |
| Placebo Control | 5 (27.78%) | 13 (72.22%) | 18 |
| Total | 5 | 31 | 36 |

The vaccinate group showed a statistically significant lower proportion of animals with reproductive tissue infection compared to the placebo control group (p=0.0455; Fisher's Exact Test).

Preventive Fraction for reproductive tissue Infection is presented in Table 12.

TABLE 12

Preventive Fraction and Lower and Upper 95% Confidence Bounds of Morbid Calves by Reproductive Tissue Infection[1]

| Total Number | | Morbid per Group | | Preventive Fraction | Confidence Bound | |
|---|---|---|---|---|---|---|
| Vaccines | Controls | Vaccines | Controls | | Lower | Upper |
| 18 | 18 | 0 | 5 | 1.00 | 0.23 | 1.00 |

[1]Reproductive tissue positive for infection post challenge

Preventive Fraction was 1.00 (LCB=0.23) for the vaccine group.

Secondary Outcome Results

One animal had three days of positive observations for depression with all positive observations occurring prior to challenge. There were no other positive secondary outcomes observed for any animal (i.e. inappetance/anorexia, jaundice, diarrhea or conjunctivitis). No additional analyses were performed.

CONCLUSIONS

*L. hardjo Bovis* is considered a host-adapted leptospiral species in cattle, which can establish persistent infections in cattle of any age through colonization of renal and reproductive tissues. Infected cattle have a high potential of shedding the organism through bodily fluids (primarily urine) as well as developing reproductive disease generally in the form of reduced conceptions rates. With respect to these clinical characteristics, the primary outcomes used for analysis of efficacy in this study were leptospiral urine shedding and colonization of kidney and reproductive tract tissues.

The challenge model used in this study was effective in establishing morbidity as evident by the infection and colonization of renal and reproductive tract tissues in the placebo vaccinated animals. The incidence of *L. hardjo-bovis* reisolation from urine samples of placebo vaccinated calves was 100% (Table 7). Subsequent reisolation of *L. hardjo-bovis* from kidney tissue was 100% for this group as well (Table 9). Infection and colonization of reproductive tract tissues was evident as *L. hardjo-bovis* was, isolated from 27.78% the placebo vaccinated animals (Table 11). The challenge model was therefore considered effective in establishing morbidity in 100% of the placebo vaccinated animals and provided an effective model for evaluating efficacy.

Efficacy was observed in the vaccine group 12 months following the second vaccination. The vaccine group demonstrated a statistically significant reduction in total morbidity (urine shedding, renal and reproductive tract tissue colonization) when compared to the placebo group (Tables 3, 9 and 11). The estimation of Preventive Fraction for morbidity of the vaccine group supports efficacy.

The impact of efficacy on morbidity is evident in the kidney and reproductive tract where colonization was significantly reduced for the vaccine group with no reisolation occurring (Tables 9 and 11).

These data demonstrate the 12 month duration of immunity afforded by vaccination with the L. hardjo-bovis vaccines.

The protective immunity provided the by experimental vaccines in this study significantly reduced leptospiral urinary shedding and significantly reduced or eliminated kidney and reproductive tract colonization.

While example compositions, methods, and so on have been illustrated by description, and while the descriptions are in considerable detail, it is not the intention of the applicants to restrict or in any way limit the scope of the application. It is, of course, not possible to describe every conceivable combination of components or methodologies for purposes of describing the compositions, methods, and so on described herein. Additional advantages and modifications will readily appear to those skilled in the art. Therefore, the disclosure is not limited to the specific details, the representative apparatus, and illustrative examples shown and described. Thus, this application is intended to embrace alterations, modifications, and variations that fall within the scope of the application. Furthermore, the preceding description is not meant to limit the scope of the invention. Rather, the scope of the invention is to be determined by the appended claims and their equivalents.

The invention claimed is:

1. A method for stimulating an immune response effective against *Leptospira* in bovine animals, comprising:
   administering to a bovine animal, at between 4 to 26 weeks of age, a composition that includes an immunogenic amount of inactivated *Leptospira borgpetersenii*, serovar *hardjo*, type *hardjo-bovis*, (*L. hardjo-bovis*) and optionally an adjuvant,
   wherein the administering stimulates an immune response specific for *L. hardjo-bovis* in the animal and wherein said immune response persists for about one year.

2. The method of claim 1, wherein the administering to animals between 4 to 26 weeks of age is followed, within about 4 weeks later, by a second administering of an immunogenic amount of inactivated *L. hardjo-bovis*.

3. The method of claim 1, wherein said administering is done to reduce chronic leptospirosis.

4. The method of claim 1, wherein the composition includes additional components, including one or more of inactivated *Leptospira interrogans*, serovars *canicola*, *grippotyphosa*, *icterohaemorrhagiae* and *pomona*, inactivated *Campylobacter fetus*, inactivated *Histophilus somni*, inactivated bovine virus diarrhea type 1, inactivated bovine virus diarrhea type 2, inactivated parainfluenza type 3, inactivated bovine respiratory syncytial virus and inactivated bovine herpes virus-1.

5. A method, comprising:
   administering to cattle between 4 to 26 weeks of age, a composition that includes an immunostimulatory amount of inactivated *Leptospira borgpetersenii*, serovar *hardjo*, type *hardjo-bovis*, (*L. hardjo-bovis*) and optionally an adjuvant,
   wherein if said cattle are exposed to a pathogenic amount of *L. hardjo-bovis* about 56 weeks subsequent to the administering, or later, said exposed cattle have a reduced rate of *L. hardjo-bovis* morbidity as compared to cattle that have not been administered the composition and are exposed to the pathogenic amount of *L. hardjo-bovis*.

6. The method of claim 5, wherein the composition includes inactivated *Leptospira interrogans* of one or more serovars *canicola*, *grippotyphosa*, *icterohaemorrhagiae* and *pomona*.

7. The method of claim 5, wherein the composition includes one or more of inactivated *Campylobacter fetus*, inactivated *Histophilus somni*, inactivated bovine virus diarrhea type 1, inactivated bovine virus diarrhea type 2, inactivated parainfluenza type 3, inactivated bovine respiratory syncytial virus and inactivated bovine herpes virus-1.

8. The method of claim 5, wherein the administering to cattle between 4 to 26 weeks of age is followed, within about 4 weeks later, by a second administering of the immunostimulatory amount of inactivated *L. hardjo-bovis*.

9. The method of claim 5, wherein *L. hardjo-bovis* morbidity includes detection of *L. hardjo-bovis* in samples of one or more of blood, urine or tissue from the cattle.

10. A method for reducing the morbidity associated with *Leptospira hardjo-bovis* in bovines, comprising:
    administering twice to bovines of age 4 to 26 weeks, an adjuvanted composition of killed *Leptospira borgpetersenii*, serovar *hardjo*, type *hardjo-bovis*, (*L. hardjo-bovis*) to produce an immune response specific for *L. hardjo-bovis* in the bovines,
    wherein if the bovines are exposed to *L. hardjo-bovis* subsequent to the administering, detection of *L. hardjo-bovis* in the tissue is at least 25% less likely, for at least one year subsequent to the first administering, than in the tissue of bovines that have not been administered the composition and are exposed to *L. hardjo-bovis*.

11. The method of claim 10, wherein if the bovines are exposed to *L. hardjo-bovis* subsequent to the administering, detection of *L. hardjo-bovis* in the tissue is at least 40% less likely, for at least one year subsequent to the first administering, than is detection of *L. hardjo-bovis* in the tissue of bovines that have not been administered the composition and are exposed to *L. hardjo-bovis*.

12. The method of claim 10, wherein if the bovines are exposed to *L. hardjo-bovis* subsequent to the administering, detection of *L. hardjo-bovis* in the tissue is at least 50% less likely, for at least one year subsequent to the first administering, than is detection of *L. hardjo-bovis* in the tissue of bovines that have not been administered the composition and are exposed to *L. hardjo-bovis*.

13. A method for reducing the morbidity associated with *Leptospira hardjo-bovis* in bovines, comprising:
    administering twice to bovines an adjuvanted composition of killed *Leptospira borgpetersenii*, serovar *hardjo*, type *hardjo-bovis*, (*L. hardjo-bovis*) to produce an immune response specific for *L. hardjo-bovis* in the bovines,
    wherein if the bovines are exposed to *L. hardjo-bovis* subsequent to the administering, detection of *L. hardjo-bovis* in the tissue is at least 25% less likely, for at least one year subsequent to the first administering, than in the tissue of bovines that have not been administered the composition and are exposed to *L. hardjo-bovis*, wherein administering twice means a first administering at approximately age 4 weeks, and a second administering at approximately age 8 weeks.

14. The method of claim 13, wherein the frequency of one or more of abortions, stillbirths or birth of weak calves is less in bovines administered the adjuvanted composition than in bovines not administered the adjuvanted composition.

15. The method of claim 5, further comprising:

a first administering to bovine animals between 4 to 26 weeks of age, and a second administering within about 4 to 8 weeks later, of a composition that includes an immunostimulatory amount of inactivated *L. interrogans* serovars *canicola, grippotyphosa, icterohaemorrhagiae* and *pomona*, inactivated *Campylobacter fetus*, inactivated bovine virus diarrhea type 1, inactivated bovine virus diarrhea type 2, inactivated parainfluenza type 3, inactivated bovine respiratory syncytial virus, and inactivated bovine herpes virus-1, in addition to the *Leptospira borgpetersenii*, serovar *hardjo*, type *hardjo-bovis* (*L. hardjo-bovis*), wherein an immune response effective against *L. hardjo-bovis* is stimulated in the animals, and wherein if the animals are exposed to a pathogenic amount of *L. hardjo-bovis* about 56 weeks subsequent to the first administering, or later, the exposed animals have a reduced rate of *L. hardjo-bovis* morbidity as compared to animals that have not been administered the composition and are exposed to the pathogenic amount of *L. hardjo-bovis*.

16. The method of claim 15, wherein reduced rate of *L. hardjo-bovis* morbidity as compared to animals that have not been administered the composition means that detection of *L. hardjo-bovis* in animals administered the composition, at a time after they were exposed to the pathogenic amount of *L. hardjo-bovis*, is less frequent as compared to the animals that have not been administered the composition.

17. The method of claim 16, wherein the detection of *L. hardjo-bovis* is performed by: i) culturing of *L. hardjo-bovis* from urine, blood, kidney or reproductive tissue, and/or ii) fluorescent antibody detection of *L. hardjo-bovis* in urine.

18. The method of claim 16, wherein the detection of *L. hardjo-bovis* in animals administered the composition, at a time after they were exposed to the pathogenic amount of *L. hardjo-bovis*, is at least 61 percentage points or at least 72 percentage points or at least 78 percentage points less frequent as compared to the animals that have not been administered the composition.

19. The method of claim 15, wherein a Preventive Fraction calculated from the method is at least 0.72 or at least 0.92 or 1.

20. The method of claim 15 wherein the first administering is at 4 weeks of age.

* * * * *